(12) United States Patent
Gagnon et al.

(10) Patent No.: US 8,511,894 B2
(45) Date of Patent: Aug. 20, 2013

(54) SYSTEM AND METHOD FOR MEASURING AND COMPENSATING FOR PATIENT PALLET DEFLECTION

(75) Inventors: Daniel Gagnon, Twinsburg, OH (US); Wenli Wang, Briarcliff Manor, NY (US)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 267 days.

(21) Appl. No.: 12/907,796

(22) Filed: Oct. 19, 2010

(65) Prior Publication Data
US 2012/0093380 A1    Apr. 19, 2012

(51) Int. Cl.
*A61B 6/04*    (2006.01)

(52) U.S. Cl.
USPC .......................................... 378/205; 382/131

(58) Field of Classification Search
None
See application file for complete search history.

(56) References Cited

U.S. PATENT DOCUMENTS

| | | | |
|---|---|---|---|
| 4,761,073 | A | 8/1988 | Meltz et al. |
| 5,399,854 | A | 3/1995 | Dunphy et al. |
| 7,697,738 | B2 | 4/2010 | Da Silva et al. |
| 2010/0034435 | A1* | 2/2010 | Kariv .............................. 382/128 |
| 2010/0040197 | A1* | 2/2010 | Maniawski et al. .............. 378/65 |

FOREIGN PATENT DOCUMENTS
WO    WO2010046602    *    4/2010

OTHER PUBLICATIONS

Lamare et al, List-mode-based reconstruction for respiratory motion correction in PET using non-rigid body transformations, Mar. 2007, Phys. Med. Biol. 52 (2007) 5187-5204.*
Wikipedia, the free encyclopedia, Affine Transformation, Oct. 15, 2010.*
Malla et al., "A Special Fiber Optic Sensor for Measuring Wheel Loads of Vehicles on Highways," Sensors 2008, 8, pp. 2551-2568, Apr. 11, 2008.

* cited by examiner

*Primary Examiner* — Stephen R Koziol
*Assistant Examiner* — Raphael Schwartz
(74) *Attorney, Agent, or Firm* — Oblon, Spivak, McClelland, Maier & Neustadt, L.L.P.

(57) ABSTRACT

A PET imaging system includes a measurement subsystem, a data acquisition subsystem, and a reconstruction subsystem. The measurement subsystem detects deflection in a patient pallet, and generates deflection information based on the detected deflection. The data acquisition subsystem receives the deflection information from the measurement subsystem and PET measurement data corresponding to a plurality of coincidence events from a PET scanner, and communicates the received deflection information and PET measurement data to the reconstruction subsystem. The reconstruction subsystem includes a processor that reconstructs a PET scan image using the deflection information and the PET measurement data communicated by the data acquisition subsystem.

19 Claims, 10 Drawing Sheets

SYSTEM AND METHOD FOR MEASURING AND COMPENSATING FOR PATIENT PALLET DEFLECTION

BACKGROUND OF THE INVENTION

1. Field

Embodiments described herein relate generally to a method of reconstructing a positron emission tomography (PET) scan image, and a PET imaging system for performing the same. Specifically, embodiments described herein relate generally to reconstructing a PET scan image that accounts for deflection in a patient pallet or bed.

2. Background

PET imaging is growing in the field of medical imaging. PET imaging starts with the administration of a radiopharmaceutical into a patient. The radiopharmaceutical is mostly injected into the patient, but can also be inhaled or ingested. After administration of the radiopharmaceutical, in time, the physical and bio-molecular properties of the agent will cause it to concentrate at specific locations in the human body. The actual spatial distribution of the agent, the intensity of the point or region of accumulation, and the kinetics of the process from administration to capture to eventually elimination are all elements that may have a clinical significance. During this process, a positron emitter attached to the radiopharmaceutical agent, will emit positrons according to the physical properties of the isotope, such as half-life, branching ratio, etc.

When an emitted positron collides with an electron, an annihilation event occurs, and as a result the positron and electron are destroyed. Most of the time, the annihilation event produces two gamma rays (at 511 keV) traveling at substantially 180° apart.

By detecting the two gamma rays, and drawing a line between their locations, i.e., the line-of-response (LOR), one can retrieve the likely location of the original disintegration. While this process will only identify a line of possible interaction, by accumulating a large number of those lines, and through a tomographic reconstruction process, the original distribution can be estimated. In addition to the location of the two scintillation events resulting from the interaction of the two gamma rays in scintillator crystals, if accurate timing (within a few hundred picoseconds) is available, a time-of-flight (TOF) calculation can add more information on the likely position of the event along the line. Limitations in the timing resolution of the scanner will determine the accuracy of the positioning along this line. Further, limitations in the determination of the location of the original scintillation events will determine the ultimate spatial resolution of the scanner, while the specific characteristics of the isotope (e.g., energy of the positron) will also contribute (via positron range and co-linearity of the two gamma rays) to the determination of the spatial resolution this specific agent.

The collection of a large number of events creates the necessary information for an image of an object to be estimated through tomographic reconstruction. Two detected events occurring at substantially the same time at corresponding detector elements form a line-of-response that can be histogrammed according to their geometric attributes to define projections, or sinograms to be reconstructed. Events can also be added to the image individually.

The fundamental element of the data collection and image reconstruction is therefore the LOR, which is the line traversing the system-patient aperture. Additional information can be obtained regarding the location of the event. First, it is known that, through sampling and reconstruction, the ability of the system to reconstruct or position a point is not space-invariant across the field of view, but is better in the center, slowly degrading toward the periphery. A point-spread-function (PSF) is typically used to characterize this behavior. Tools have been developed to incorporate the PSF into the reconstruction process. Second, the time-of-flight, or time differential between the arrival times of the gamma ray on each detector involved in the detection of the pair, can be used to determine where along the LOR the event is more likely to have occurred.

The above described detection process must be repeated for a large number of events. While each imaging case must be analyzed to determine how many counts (i.e., paired events) are required to support the imaging tasks, current practice dictates that a typical 100-cm long, FDG (fluorodeoxyglucose) study will need to accumulate several hundred millions counts. The time required to accumulate this number of counts is determined by the injected dose and the sensitivity and counting capacity of the scanner.

PET imaging systems use detectors positioned across from one another to detect the gamma rays emitting from the object. Typically a ring of detectors is used in order to detect gamma rays coming from each angle. Thus, a PET scanner is typically substantially cylindrical to be able to capture as much radiation as possible, which should be, by definition, isotropic. The use of partial rings and rotation of the detector to capture missing angles is also possible, but these approaches have severe consequences for the overall sensitivity of the scanner. In a cylindrical geometry, in which all gamma rays included in a plane have a chance to interact with the detector, an increase in the axial dimension has a very beneficial effect on the sensitivity or ability to capture the radiation. Thus, the best design is that of a sphere, in which all gamma rays have the opportunity to be detected. Of course, for application to humans, the spherical design would have to be very large and thus very expensive. Accordingly, a cylindrical geometry, with the axial extent of the detector being a variable, is realistically the starting point of the design of a modern PET scanner.

Once the overall geometry of the PET scanner is known, another challenge is to arrange as much scintillating material as possible in the gamma ray paths to stop and convert as many gamma rays as possible into light. In order to be able to reconstruct the spatio-temporal distribution of the radio-isotope via tomographic reconstruction principles, each detected event will need to be characterized for its energy (i.e., amount of light generated), its location, and its timing. Most modern PET scanners are composed of several thousand individual crystals, which are arranged in modules and are used to identify the position of the scintillation event. Typically crystal elements have a cross section of roughly 4 mm×4 mm. Smaller or larger dimensions and non-square sections are also possible. The length or depth of the crystal will determine how likely the gamma ray will be captured, and typically ranges from 10 to 30 mm. The detector module is the main building block of the scanner.

PET imaging relies on the conversion of gamma rays into light through fast and bright scintillation crystals. After determining the interaction position in the scintillator and time pairing of individual events, the location of the annihilation process can be recreated. These actions require very fast components—detector and electronics—and they also require excellent signal to noise ratio. With high quality electronics, the signal to noise ratio is mainly determined by the inherent Poisson statistics involved in the detection process. Detecting more photons will result in improved signal-to-noise-ratio, and, therefore, better spatial and timing resolution. No improvement in detector design and electronics can compensate for significant loss of light in the detection process. The fraction of the total amount of light collected (relative to the amount created in the scintillator) is a good measure of the efficiency of the design. So to maximize the amount of light collected, one would try to get the light sensor as close as possible to the scintillation crystal and avoid reflections and other edge effects. This would then force the arrangement to be a large array detector with a short distance between crystal and sensor.

As described above, a PET imaging system is more than just a counter and, in addition to detecting the presence of a scintillation event, the system must identify its location. Conceptually, perhaps the most straightforward design to allow identification of the location of each interaction is to have a separate photosensor and data acquisition channel for each scintillator crystal. Due to constraints such as the physical size of common photosensors, the power required for each data acquisition channel, and the associated cost of these items, some form of multiplexing is usually used to reduce the number of photosensors and channels of electronics. The two most common forms of multiplexing are optical multiplexing (light sharing) or analog electronic multiplexing (resistive charge-sharing networks).

A substantial effort is made to properly locate each and every event in space and time. A series of additional corrections will compensate for the slight non-ideal conditions of the imaging system. For instance, sensitivity correction will address the minute differences in the individual crystals, gain correction will compensate for the slight intrinsic gain differences of the photomultiplier tubes (PMTs), a complex system matrix can account for small gaps in the crystal arrangement in the detector ring, etc. However, the effects of those non-ideal conditions on the imaging system are all of lesser significance than the affect of possible patient motion.

Patient motions can be managed to some degree via instructions and stabilization straps. However, deflections in the patient pallet are inherent to the design of the scanner. The mechanical properties of the patient pallet (e.g., sagging, deflection, bending, etc.) can affect image quality if it becomes too severe. For example, these mechanical properties may result in vertical misalignment between successive incremental PET scans, or between scans by a CT scanner and a PET scanner in a PET/CT imaging system. While the patient pallet is typically designed to minimize deflection, a shift of several millimeters can occur in most imaging systems. This shift may result in possible departure from the optimal image quality of the scanner.

Accordingly, one possible approach to addressing the effects of deflection is to compensate for any deflection at the patient pallet design level. However, building a rigid enough system to minimize the deflection of the patient pallet would result in increases in cost and complexity of the patient pallet. In addition, existing machines may not be suited for refitting with the redesigned patient pallet, since those machines might not be capable of incorporating the new mechanical components that will be required.

Image-based measurement and compensation is another approach to addressing the deflection effects. For instance, in CT imaging, the image itself can be used to estimate the amount of deflection of the patient pallet, and therefore provide the imaging system with all the necessary correction information. In a PET imaging system, however, the spatial resolution is much lower and is at best 4 to 5 mm. Further, the spatial resolution decreases away from the center of the PET scanner. Where the structure of the patient pallet could be visible, spatial resolution could be as large as 10 mm. This progressive degradation from rays emitted off axis are due, for example, to parallax and depth of interaction. For example, rays emitted from the center of the PET scanner would interact with the 4×4 mm face of the crystal. However, the same rays, when off-center, would "see" a larger crystal (e.g., the oblique part of a 12 mm long crystal). Such a spatial resolution would make it extremely difficult to use a PET scan image induced measurement of the deflection at the imaging PET area. In addition, the patient pallet would not be visible to the PET imaging system unless radioactive sources are attached to the patient pallet surface.

In a PET/CT imaging system, it would theoretically be possible to measure the deflection in the CT imaging space and to extrapolate the deflection in the PET imaging space, which is typically from 20 to 100 cm. The extrapolation would require several variables such as the patient weight and the patient's weight distribution on the table, which varies greatly. The measurements necessary to properly extrapolate the deflection value to PET from the CT field, however, appear to be as difficult to obtain as measuring the deflection itself in the PET field of view (FOV).

FIG. 1 shows an example of the effects of patient pallet deflection on a PET sagittal image. The bending (i.e., patient pallet deflection) in this figure has been exaggerated so that the effects of the deflection are more readily apparent. As illustrated in FIG. 1, the degree of deflection in the patient pallet varies depending on the area to be imaged.

BRIEF DESCRIPTION OF THE DRAWINGS

A more complete appreciation of the disclosed embodiment and many of the attendant advantages thereof will be readily obtained as the same becomes better understood by reference to the following detailed description when considered in connection with the accompanying drawings, wherein.

DETAILED DESCRIPTION

According to one embodiment, a PET imaging system includes a measurement subsystem, a data acquisition subsystem, and a reconstruction subsystem. The measurement subsystem is configured to detect deflection in a patient pallet, and to provide deflection information based on the detected deflection. The data acquisition subsystem is configured to receive the deflection information from the measurement subsystem and PET measurement data corresponding to a plurality of coincidence events from a PET scanner, and to communicate the received deflection information and PET measurement data to the reconstruction subsystem. The reconstruction subsystem includes a processor that is configured to reconstruct a PET scan image using the deflection information and the PET measurement data communicated by the data acquisition subsystem.

Embodiments described herein relate to a system and method for compensating for deflection in a patient pallet of a PET imaging system in order to generate a PET image as if it had been acquired on a perfectly rigid system. By compensating for the effects of the deflection in the patient pallet, a PET scan image of high image quality that is independent of a patient's weight and weight distribution on the patient pallet can be provided. Further, compensating for the deflection facilitates the alignment of the PET scan image with a corresponding CT image, as well as generating a PET scan image that is referenced to an absolute reference point.

Accordingly, embodiments include descriptions of a system that is capable of determining patient pallet deflection on a per-patient basis, and a method to use the deflection information to compensate for the deflection in the PET image processing chain.

Figure 1:
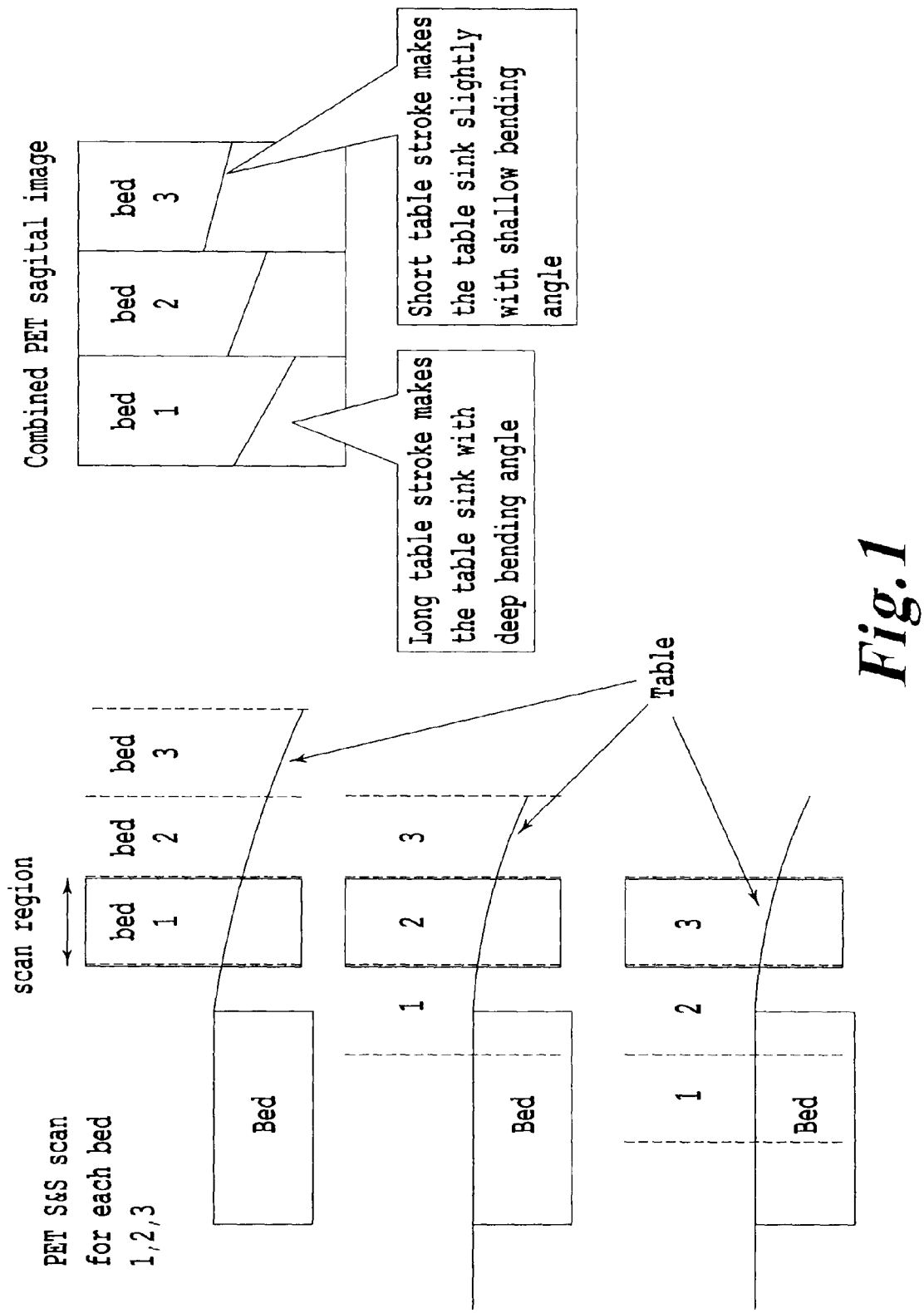
FIG. 1 illustrates an example of the effects of bending on a patient pallet in a PET imaging system.
Figure 2A:
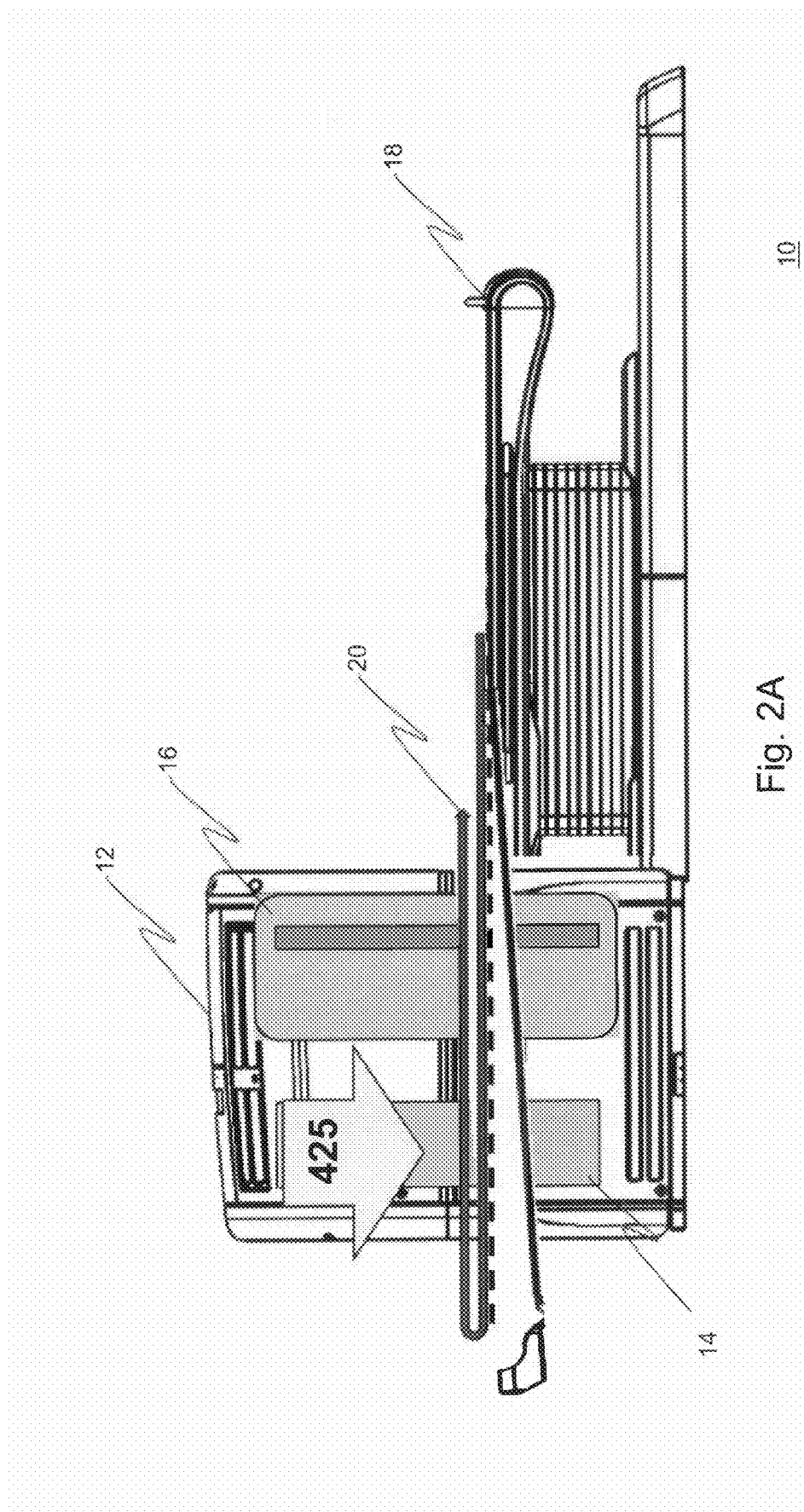
FIG. 2A illustrates an embodiment of a PET imaging system.

FIG. 2A illustrates an embodiment of a PET imaging system 10. The PET imaging system 10 includes an assembly 12 on which a PET scanner 14 and a CT scanner 16 (optional) are mounted. The CT scanner 16 is optional and is excluded in other embodiments of the PET imaging system 10. The PET imaging system 10 further includes a patient pallet 18 and an optical fiber 20 that is used to detect deflection in the patient pallet 18. By using the optical fiber 20, a longitudinal measurement system is provided to measure the pallet deflection. In one embodiment, the optical fiber 20 is fixed to the side of the patient pallet 18. In other embodiments, the optical fiber 20 is attached to other surfaces of or embedded into, the patient pallet 18. The optical fiber 20 may be placed anywhere on or within the patient pallet 18 as long as interaction with patient surfaces and the patient pallet mechanism (e.g., rollers, supports, etc.) is avoided.

Figure 2B:
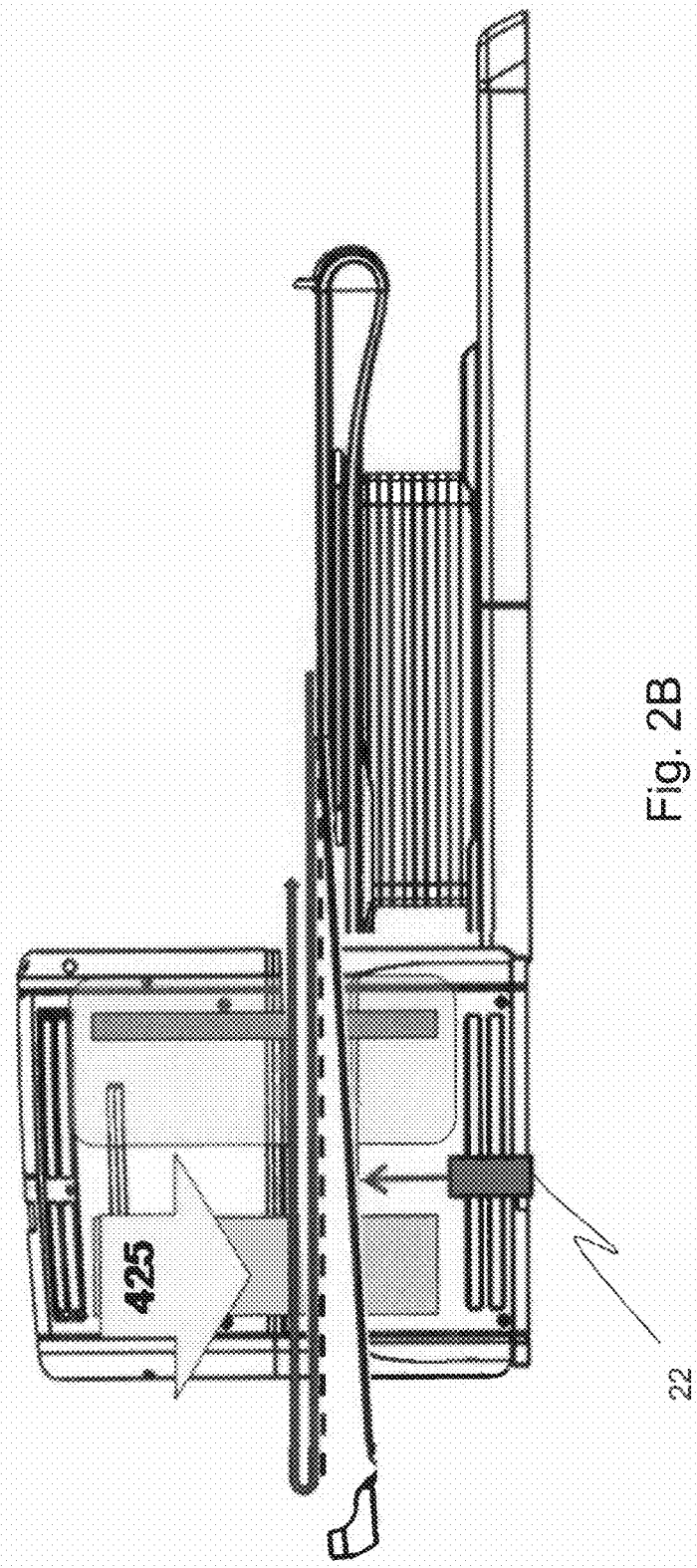
FIG. 2B illustrates another embodiment of the PET imaging system.

Further, one or more optical fibers 20 may be used to detect deflection in the patient pallet 18. Alternatively, one or a combination of other sensors, such as a laser, an encoder with a string or bar code, etc., may be used in place of, or to supplement, the optical fiber 20. The use of other sensors, however, typically require that measurements be made in a plane perpendicular to the movement of the patient pallet. FIG. 2B illustrates one example in which the optical fiber 20 is supplemented with a laser 22 positioned below the patient pallet 18. In this example, the laser 22 is located between the PET scanner 14 and CT scanner 16. The location of the laser, however, is not limited to this location and may be placed outside the assembly 12. Further, in other embodiments, the laser 22 is placed in other location such as to the side (e.g., perpendicular to FIG. 2B) or above the patient pallet 18.

Figure 3A:
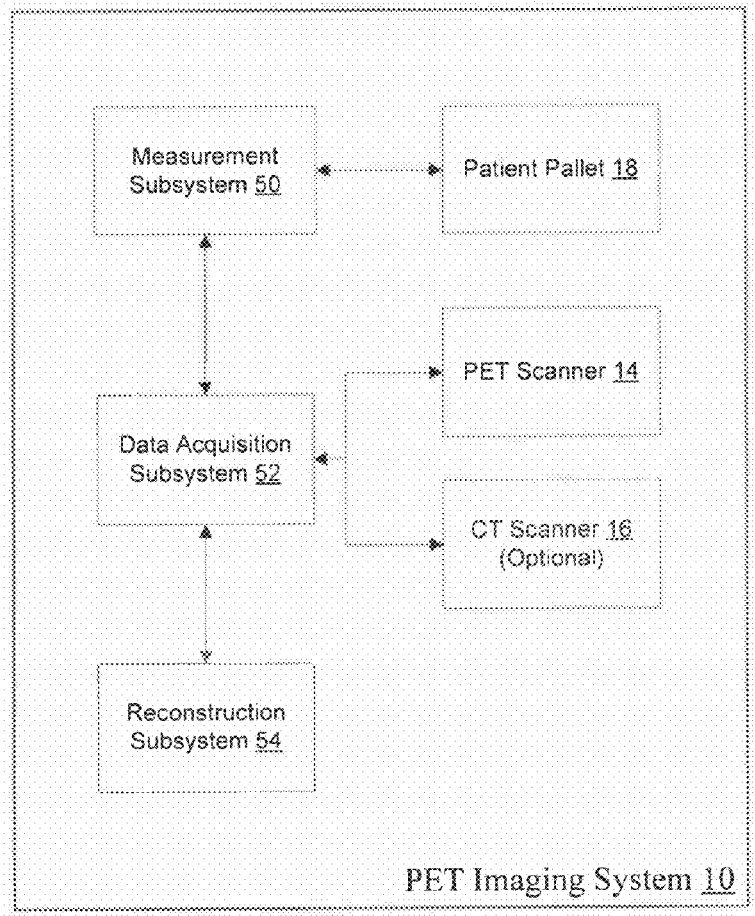
FIG. 3A is a block diagram of the main components of the PET imaging system in an exemplary embodiment.

FIG. 3A is a block diagram of the main components of the PET imaging system 10, in one embodiment. The PET imaging system 10 includes a measurement subsystem 50, a data acquisition subsystem 52, a reconstruction subsystem 54, the patient pallet 18, the PET scanner 14, and the CT scanner 16 (optional).

Figure 3B:
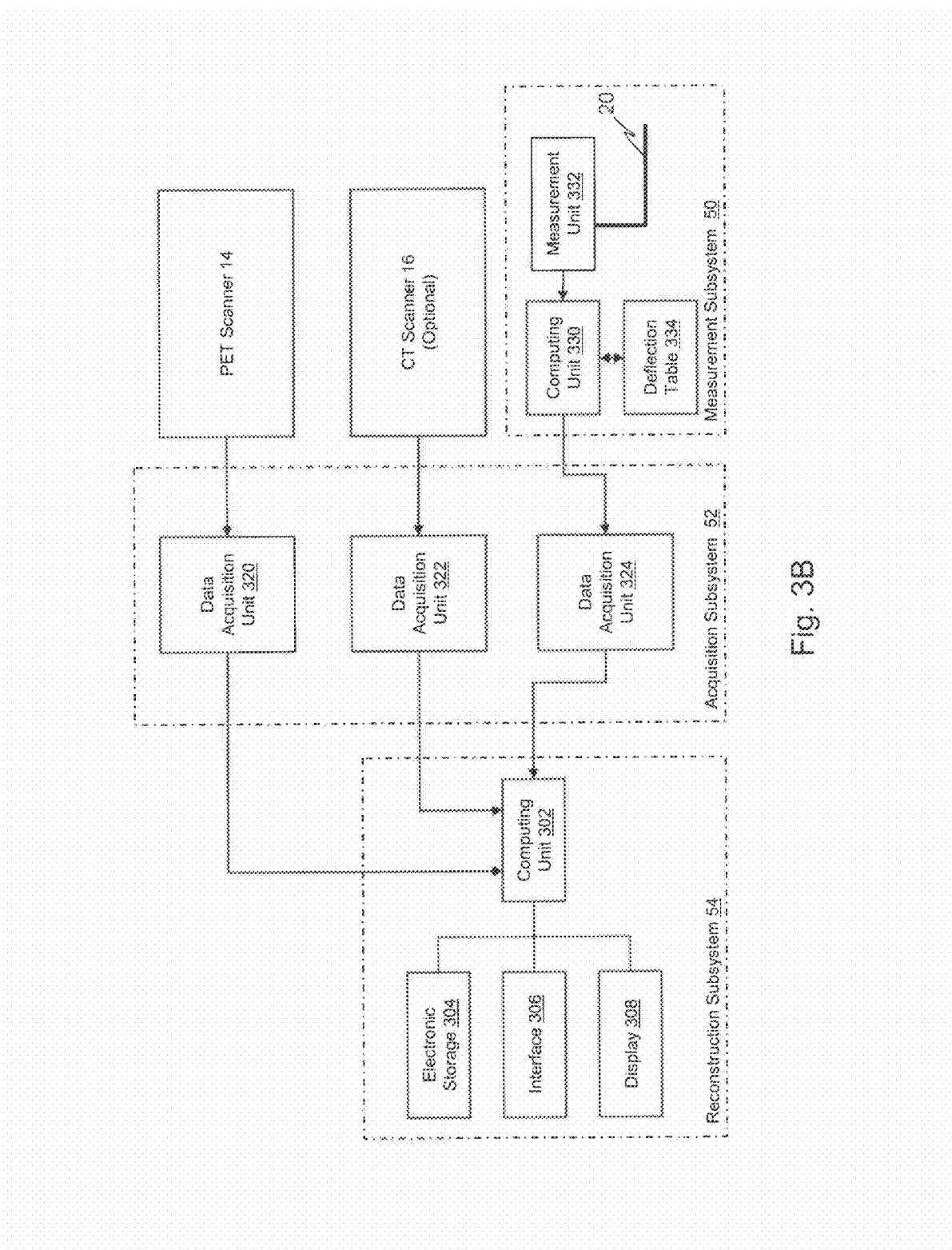
FIG. 3B is a more detailed schematic drawing of the subsystems included in a PET imaging system according to an exemplary embodiment of the present invention.

FIG. 3B is a more detailed schematic drawing of the subsystems included in the PET imaging system 10, according to an exemplary embodiment. As illustrated in FIG. 3B, the acquisition subsystem 52 acquires data from the PET scanner 14, the CT scanner 16 (optional), and the measurement subsystem 50, and provides the data to the reconstruction subsystem 54. The acquisition subsystem 52 acquires and provides the data via one or more wired and/or wireless communication methods.

The measurement subsystem 50 accurately detects the deflection of the patient pallet 18 in real time. In an exemplary embodiment, one or more optical fibers 20 and at least one measurement unit 330 that determines at least one characteristic of the optical radiation output by the one or more optical fibers 20, form the measurement subsystem 50. The at least one measurement unit 330 determines the at least one characteristic (e.g., optical radiation intensity), which is proportional to the deflection of the patient pallet 18, and provides deflection information on the at least one characteristic to a data acquisition unit 324, included in the acquisition subsystem 52. The proportionality is, for example, simple, linear, or more complex—via a model.

The deflection information is received by the data acquisition subsystem 52 either at discrete times (for a step and shoot bed motion) or at regular time intervals (for a continuous bed motion). In the exemplary embodiment, when the data acquisition subsystem 52 receives the deflection information from the measurement subsystem 50, the data acquisition subsystem 52 provides the received deflection information to the reconstruction subsystem 54 along with one or a combination of environment information on, for example, the pallet nominal height, pallet extension into the imaging aperture, other physiological signals (e.g., EKG), etc. Alternatively, the one or a combination of information may be provided to the reconstruction subsystem 54 separately. The reconstruction subsystem 54 uses the received deflection information to estimate an amount of deflection in the patient pallet 15 as a whole, or a portion thereof.

Although the data acquisition subsystem 52 illustrated in FIG. 3B also includes data acquisition units 320 and 322, which acquire data from the PET scanner 14 and the CT scanner 16, respectively, the data acquisition units do not need to be included in the same acquisition subsystem. For example, the data acquisition unit 324 may be part of a separate subsystem, or incorporated into the measurement subsystem 50 or the reconstruction subsystem 54 in other embodiments.

In one embodiment, in order to accommodate retrofitting of existing scanners, the pallet deflection measurement subsystem 50 is restricted to the patient pallet 18 only. Additional mechanisms in the actual imaging aperture are more complex to install and can also interfere with either the motion of the patient pallet 18 itself or imaging (if placed in the FOV).

Further, although the deflection information provided by the measurement subsystem 50 is discussed above as relating to at least one determined optical radiation characteristic, in another embodiment, the optical radiation itself from the one or more optical fibers 20 is provided to the acquisition subsystem 52 as deflection information, in which case the at least one measurement unit 330 is omitted from the measurement subsystem 50. In a further embodiment, as illustrated in FIG. 3B, the measurement subsystem 50 includes the one or more optical fibers 20, the at least one measurement unit 330, and a computing unit 330 that estimates the actual deflection of the patient pallet 15 as a whole, or a portion thereof, based on the at least one determined optical radiation characteristic. In one embodiment, the computing unit 330 estimates the actual deflection using a deflection table 334, which is generated during a calibration process as discussed below, in one embodiment. In this further embodiment, the measurement subsystem 50 provides the estimated deflection as deflection information to the acquisition subsystem 52.

The measurement subsystem 50 of the disclosed embodiments may also include one or a combination of the other sensors discussed above. Alternatively, the one or a combination of the other sensors can replace the one or more optical fibers 20. Additionally, as noted above, the measurement subsystem 50 may provide the deflection information (e.g., the at least one determined characteristic of the optical irradiation) via wired and/or wireless communication methods. Further, the deflection information is provided directly to the reconstruction subsystem 54, instead of through the acquisition subsystem 52, in other embodiments.

One system that can be used to implement the measurement subsystem 50 uses the Bragg interference principle to detect deflection in the patient pallet 18. In one embodiment, the measurement subsystem 50 includes one or more optical fibers 20 that are fixed alongside the patient pallet 18. The one or more optical fibers 20 can be arranged on the patient pallet 18 itself, with negligible impact on either CT or PET imaging. In an exemplary embodiment, deflection in the patient pallet 18 causes the one or more optical fibers 20 to provide optical radiation having at least one characteristic that is proportional to the amount of deflection. The at least one characteristic of the optical radiation is used to determine the amount of deflection at predetermined locations of the patient pallet 18. For example, the amount of deflection at one or more predetermined locations of the patient pallet 18 is determined by monitoring differences between optical radiation sent in an optical fiber having at least one Bragg interference grating and the optical radiation reflected back through the same optical fiber. In another embodiment, the amount of deflection at predetermined locations of the patient pallet 18 is determined based on changes in the intensity of the optical radiation outputted from inner and/or outer cores, and differences in the arrival times of the optical irradiation outputted from the inner and outer cores, of a dual core FTDM optical fiber.

The measurement subsystem 50 using, for example, Bragg interference will produce a signal from one or more optical fiber 20 that is proportional to the deflection but is likely to require a calibration phase in which known deflections (or deflection measured with another system, e.g., using laser 22) would create a table of correspondence between the Bragg system and the deflection. The deflection table 334 would then be stored on the measurement subsystem 50 and used by the computing unit 330 to translate the signal to actual deflection when reporting to the acquisition subsystem 52. The deflection table may be generated automatically or manually, or may be predetermined by, for example, the manufacturer. The acquisition subsystem 52 should also be designed such that the deflection information from the measurement subsystem 50 is added to the acquired PET and/or CT measurement data at the same time as the acquisition subsystem 52 is reporting changes in the patient pallet height or longitudinal positions.

Figure 7A:
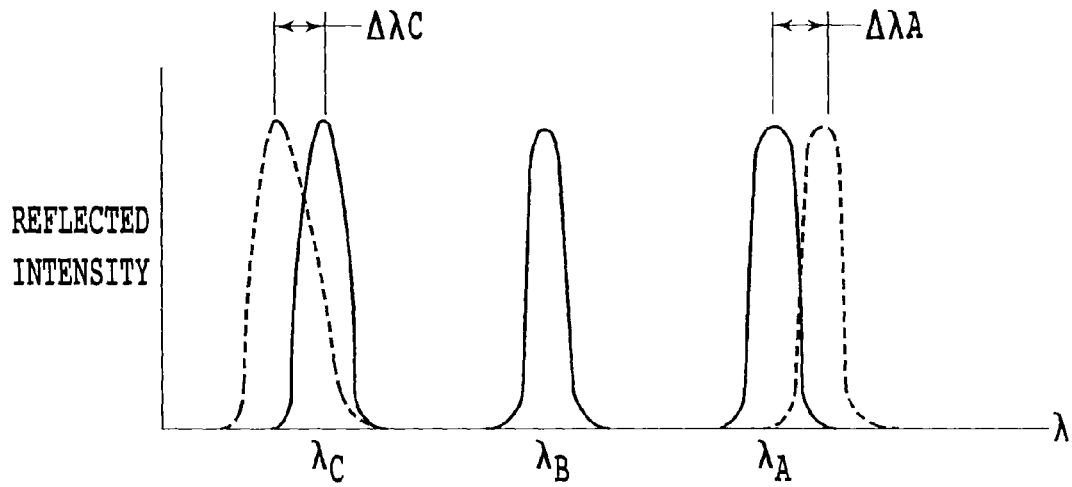
FIGS. 7A and 7B are examples of the effect on outputted light signals when an optical fiber with Bragg interference gratings and a dual core forward time division multiplexing (FTDM) optical fiber, respectively, are bent.
Figure 7B:
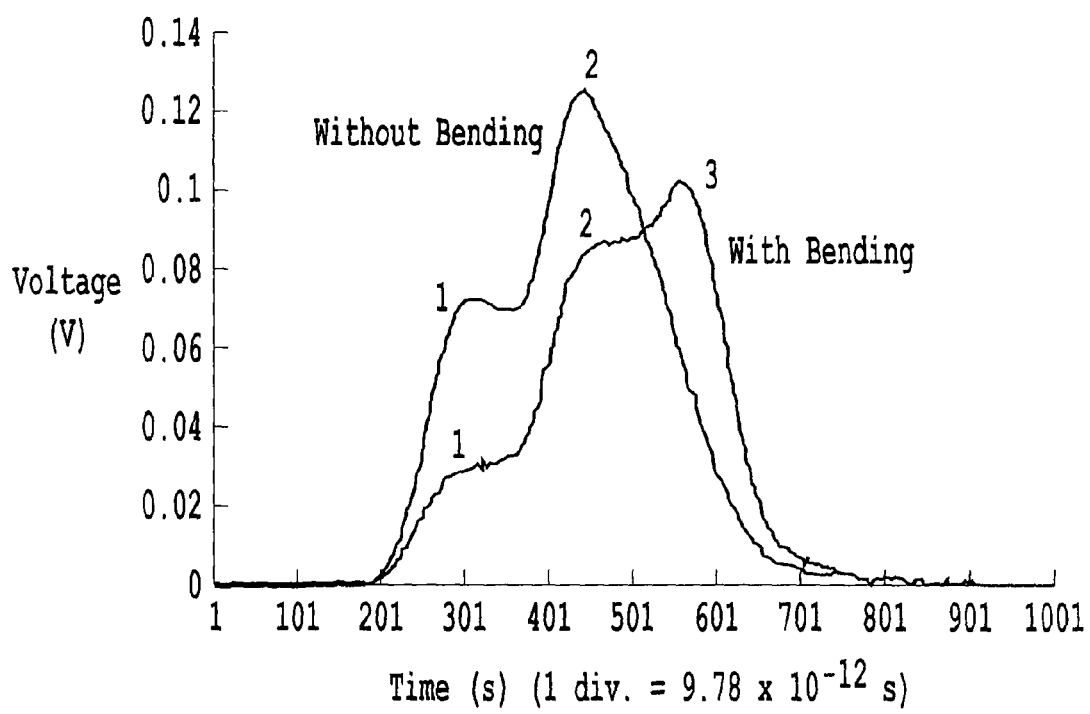

FIG. 2A illustrates how an optical fiber 20 attached to the patient pallet 18 can be used, via the Bragg interference principle, to assess deflection in the patient pallet 18, while leaving the entire patient aperture unobstructed. FIGS. 7A and 7B are examples of the effect on outputted light in an optical fiber having three Bragg interference gratings and a dual core FTDM optical fiber, respectively, when the optical fiber is bent.

Figure 4:
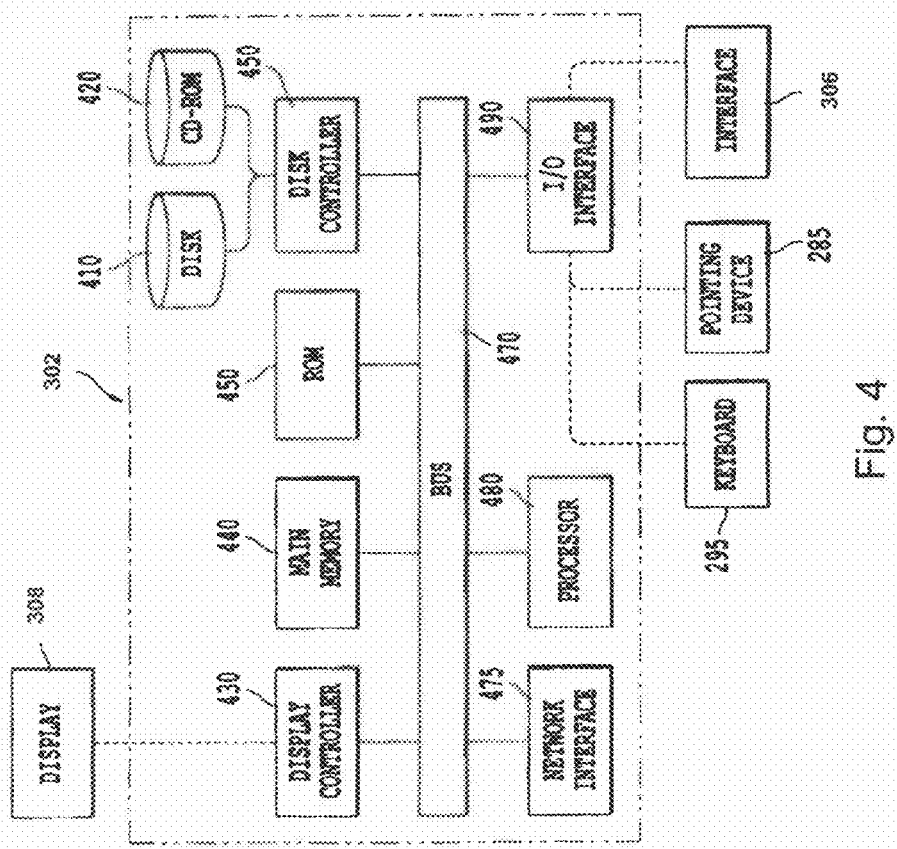
FIG. 4 is a block diagram of the computing units in the PET imaging system according to an exemplary embodiment of the present invention.

As illustrated in FIG. 3B, the reconstruction subsystem 54 includes an electronic storage 304, interface 306, display 308, and computing unit 302. The electronic storage 304 stores one or a combination of the data received from the PET scanner 14, the CT scanner 16, the measurement subsystem 50, or PET scan images reconstructed by the computing unit 302, as further discussed below. Further, the deflection table 334 is stored in the electronic storage 304 when the actual deflection in the patient pallet 18 is estimated by the reconstruction subsystem 54. The interface 306 is used to configure and/or control the computing unit 302 and/or to provide further instruction to the computing unit 302. Further, the display 308 is used by a user to operate the PET imaging system 10. FIG. 4 is a block diagram of the computing unit 302 according to an exemplary embodiment. The computing unit 302 includes a processor 480 which processes data and instructions stored in main memory 440 and/or ROM 450. The processor 480 may also process information stored on the disk 410 or CD-ROM 420. The exemplary processor 480 may be a Xeon processor from Intel of America or an Opteron processor from AMD of America. As one of ordinary skill in the art will recognize, the processor 480 may also be a Pentium processor, Core 2 Duo processor and the like. Thus, instructions corresponding to a method for gamma ray detection may be stored on any one of disk 410, CD-ROM 420, main memory 440 or ROM 450.

The computing unit 302 may also include a network interface 475, such as an Intel Ethernet PRO network interface card from Intel Corporation of America, for interfacing with a network, such as the Internet or a private network. Display controller 430 may be a NVIDIA G-Force GTX graphics adapter from NVIDIA Corporation of America for interfacing with display 385. The computing unit 302 may also include an I/O interface 490 for interfacing with a keyboard 295, pointing device 285 or other general interface 306, such as a microphone, trackball, joystick, touchscreen and the like.

Disk controller 450 interconnects disk 410, which may be a hard disk drive or FLASH memory drive, and CD-ROM 420 or a DVD drive with bus 470, which may be an ISA, ESIA, VESA, PCI, or similar for interconnecting all of the components of the computing unit 302. A description of the general features and functionality of the components of the computing unit 302 is omitted for brevity as these features are well known. Of course, other processors and hardware vendors and types known in the art may also be used with the present invention, such as Freescale Cold Fire, I. MX and ARM processors from Freescale Corporation of America.

The exemplary computing unit 302 may also be implemented separately on FPGA's, ASIC's, microcontroller, PLD's or other computer-readable mediums such as an optical disk. In addition, the exemplary computing unit 302 is a hardware platform of a computing device, such as a PC, and processor 480 may be for example an Intel Pentium Processor, or any other processor known in the art. The computer-readable instructions stored on any one of the main memory 440, ROM 450, disk 410 or CD-ROM 420 may be provided as a utility application, background daemon, or component of an operating system, or combination thereof, executing in conjunction with processor 480 and an operating system such as Microsoft VISTA, UNIX, Solaris, LINUX, Apple MAC-OS and other systems known to those skilled in the art.

Main memory 440 and/or ROM 450 supports registries and the like features of the computing unit 302. As such, main memory 440 may be a random access memory (RAM), FLASH memory, EEPROM memory, or the like, while ROM 450 is Read Only Memory, such as a PROM. Further descriptions of main memory 440 and ROM 450 are omitted for brevity as such memory is well known.

Although FIG. 4 has been described as an exemplary embodiment of the computing unit 302, the components of FIG. 4 may also be used to implement the computing unit 330, in the measurement subsystem 50, to estimate deflection in the patient pallet 18.

Figure 5:
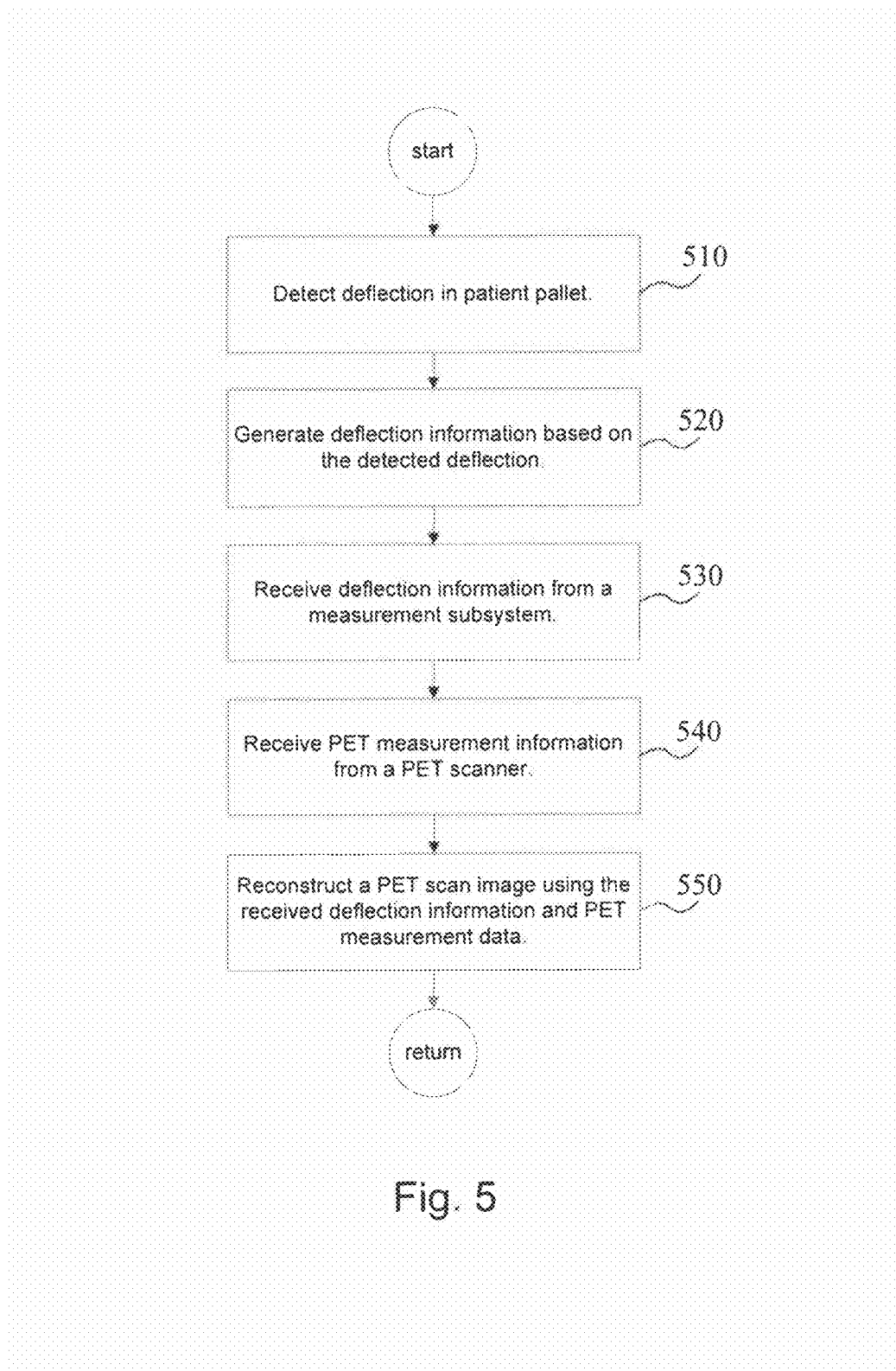
FIG. 5 is a flowchart showing the steps of a method in an embodiment of the invention.

FIG. 5 is a flowchart showing the steps for reconstructing a PET scan image while compensating for deflection in a patient pallet 18. In step 510, the deflection in the patient pallet 18 is detected. The patient pallet deflection can be detected by using the measurement subsystem 50, as discussed above. In step 520, deflection information (e.g., the optical radiation, the at least one determined optical radiation characteristic, or the estimated deflection) is provided by the measurement subsystem 50 to the acquisition subsystem 52. In one embodiment, the deflection information corresponds to at least one deflection amount at a predetermined position of the patient pallet 18. The deflection information and PET measurement data from the PET scanner 14 are received by the data acquisition subsystem 52, in steps 530 and 540. In one embodiment, the data acquisition subsystem 52 provides the deflection information along with environment information on, for example, bed nominal height, pallet extension in the imaging aperture, other physiological signals (e.g., EKG), etc., in a data flow to the reconstruction subsystem 54. The data flow also includes the PET measurement data. The inclusion of the environment information allows the reconstruction subsystem 54 to reconstruct a PET scan image with an accurate and a "contemporary" set of parameters describing the environment in which the PET measurement data is acquired. Alternatively, the deflection information may be communicated directly to the reconstruction subsystem 54 by the measurement subsystem 50. Further, a PET scan image based on the received deflection information and PET measurement data is reconstructed in step 550, by the reconstruction subsystem 54.

Figure 6A:
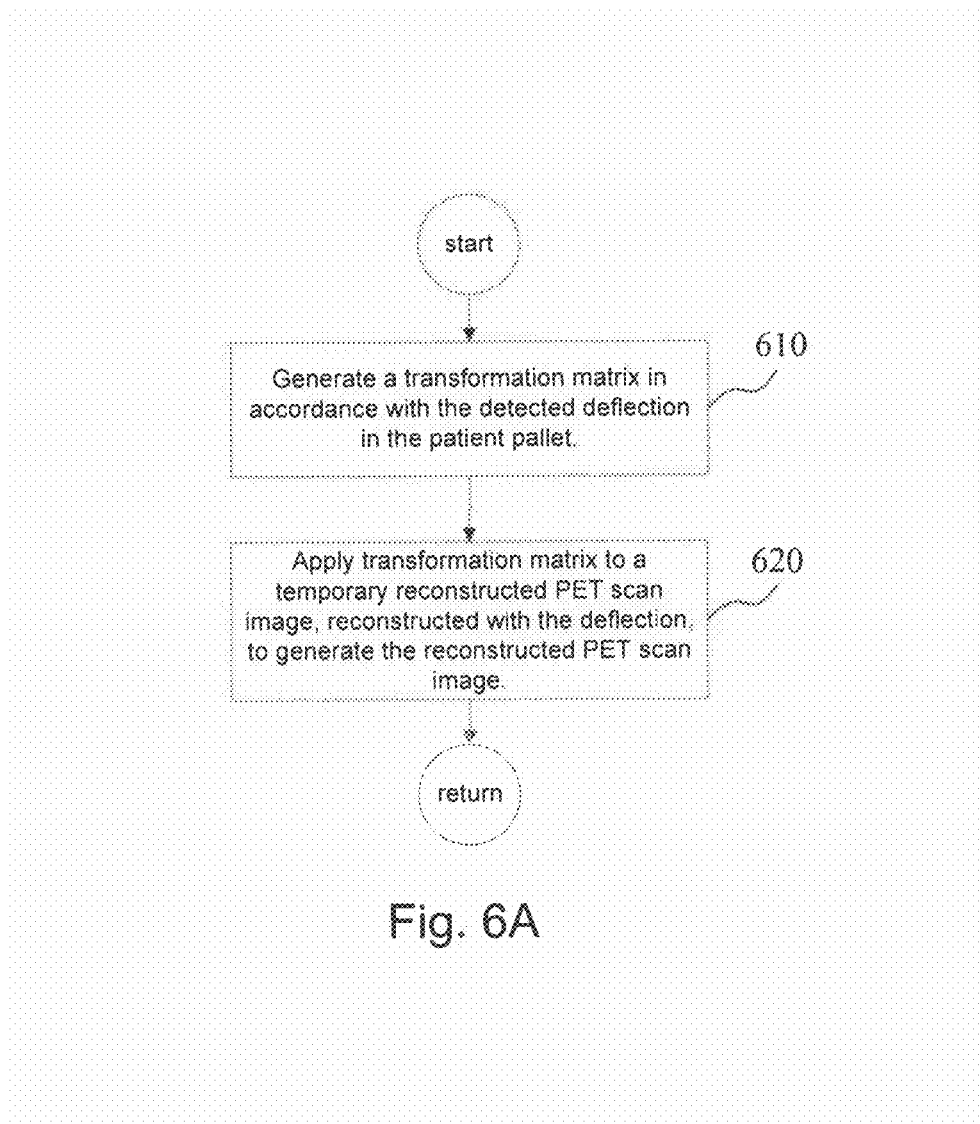
FIGS. 6A and 6B are flowcharts of different approaches to compensate for the deflection in a patient pallet.
Figure 6B:
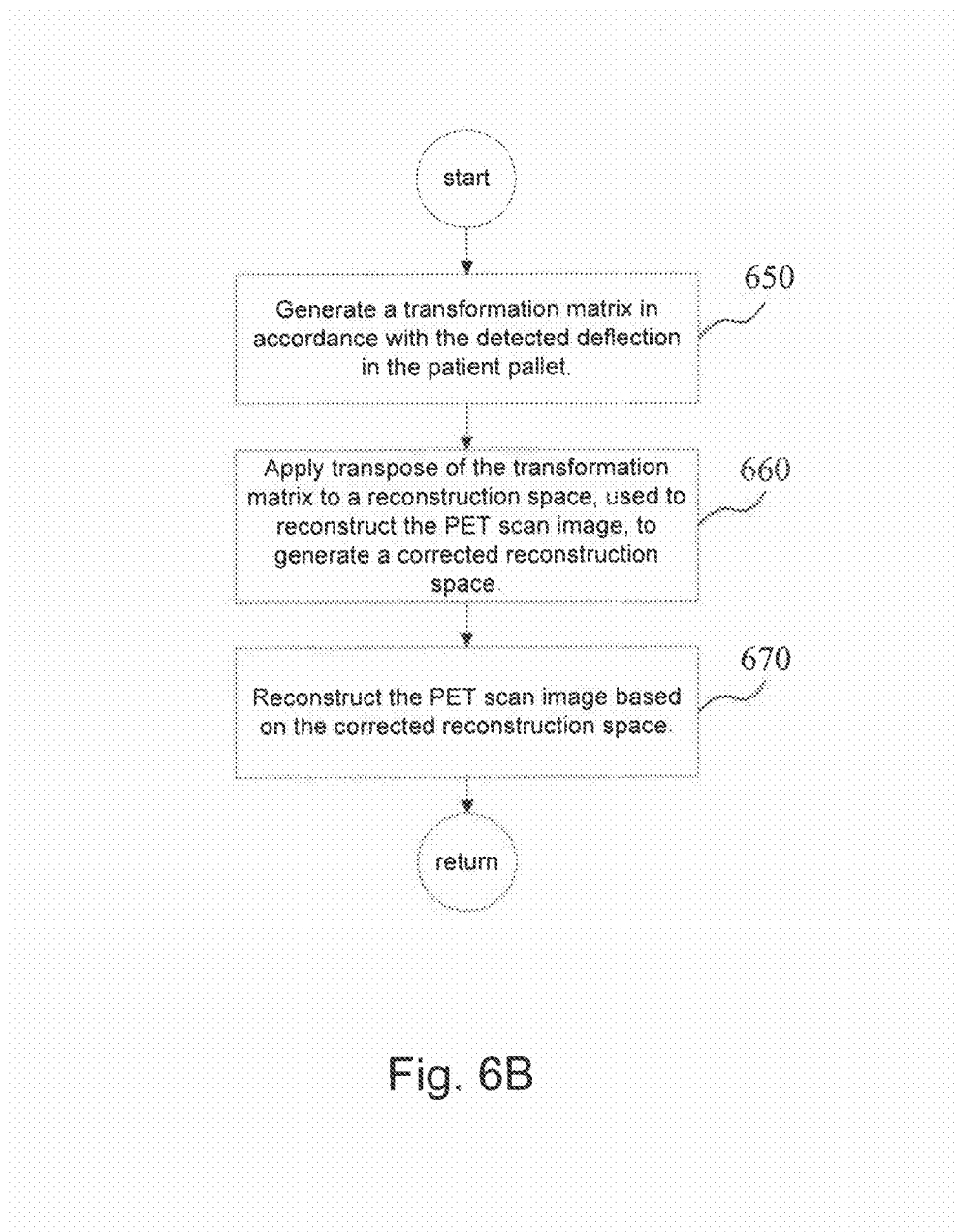

Embodiments of the method for compensating for the deflection in the patient pallet 18 will now be described. With the horizontal motion of the patient pallet 18 being monitored and reported by a patient pallet controller and the monitoring subsystem 50 providing the actual deflection amount of the portion of the patient pallet that corresponds to the area of the patient to be imaged, the complete geometry of the PET imaging system 10 illustrated in FIG. 2 is determined. After this relationship has been determined, any deflection in the patient pallet 18 is corrected by the computing unit 302 of the reconstruction subsystem 54 using one of two approaches: (1) apply a translation and rotation correction factor on the reconstructed image (as illustrated in FIG. 6A), or (2) transform the image space (as illustrated in FIG. 6B). Although, the two approaches are technically equivalent, small statistical discrepancies and/or algorithmic advantages separate the two.

Specifically, in the first approach, a PET scan image is reconstructed with the deflection and a transformation being applied to the reconstructed image. As illustrated in step 610 of FIG. 6A, a transformation matrix T is generated in accordance with the detected deflection in the patient pallet 18. Then, in step 620, the transformation matrix is applied to a temporary reconstructed PET scan image, which is reconstructed without correcting for the deflection in the patient pallet 18, to generate a corrected reconstructed PET scan image. Alternatively, using the second approach, the transformation matrix T is generated in accordance with the detected deflection in the patient pallet 18, in step 650 of FIG. 6B. Then, the transpose of the transformation matrix T, used in the first approach, is applied to the reconstruction space (or field), in step 660, so that the reconstructed data are already in the "correct" space. In step 670, a corrected reconstructed PET scan image is generated based on the corrected reconstruction space. The transformation matrix used in the transformations typically includes translation and rotation in all three axes. Alternatively, displacement or rotation known to be negligible is set to zero.

PET measurement data formation is usually modeled as $$g=Hf+b$$

where g is the measurement data, denoted as a column vector with M detector bins; f is the emission image, also denoted as a column vector with N voxels. The H is the M×N elements system matrix, denoting the probability that a positron emitted from a specific emission voxel and gets detected by a particular detector bin. The b is the background contamination, a column vector with M bins, contributed from random and scattered photons, and assumed to be known from random and scatter estimation.

In PET iterative image reconstruction, the goal is to find an estimate f that best matches the measurement data g using the above model. Note that the above reconstructed image f corresponds to the "uncorrected" patient pallet deflection space. PET image reconstruction is usually performed for one stationary bed position at a time, thus f corresponds to either one bed position in a step-and-shoot bed motion, or a particular instance of a continuous bed movement.

To obtain the emission image $f^{corr}$ in the "corrected" patient pallet deflection space, one way is to transform the uncorrected reconstructed image by $$f^{corr}=Tf$$

where T is the N×N transformation matrix, which contains both the affine transformation obtained from the measurement subsystem 50 (e.g., a fiber optics measurement subsystem) and the re-sampling of transformed coordinates that lie in between voxel grids. The transformation, in this approach, corresponds to a simple rigid translation and rotation matrix.

Another way to compensate for the patient pallet deflection is to model the deflection in the PET measurement data formation process:

$$g=HT^{-1}f^{corr}+b$$

where $T^1$ is the N×N transformation matrix, which transforms the undeflected image space into the deflected image space. Now $T^1$ can be combined with the system matrix H to form the corrected system matrix $H^{corr}$ as $$H^{corr}=HT^1$$

and $$g=H^{corr}f^{corr}+b.$$

Thus the reconstructed image will be in the undeflected image space. This approach is especially useful for continuous bed motion.

Both methods are used and substantially equivalent in the case of a step-and-shoot acquisition in which image frames exist. However, for the continuous bed movement, the incoming PET measurement data must be corrected prior to image reconstruction, since the actual deflection is continuously changing and therefore needs to be continually adjusted in the reconstruction space. Correction after image reconstruction is not compatible with the continuous bed movement, as the reconstructed image would include different amounts of deflection at multiple points in time.

While certain embodiments have been described, these embodiments have been presented by way of example only, and are not intended to limit the scope of the invention. Indeed, the novel method, computer-readable storage medium, and apparatus described herein may be embodied in a variety of other forms; furthermore, various omissions, substitutions and changes in the form of the method, computer-readable storage medium, and apparatus described herein may be made without departing from the spirit of the inventions. The accompanying claims and their equivalents are intended to cover such forms or modifications as would fall within the scope and spirit of the inventions.

The invention claimed is:

1. A positron emission tomography (PET) imaging system, comprising:
   a measurement subsystem configured to detect deflection in a patient pallet based on an optical fiber attached to the patient pallet, and to provide deflection information based on the detected deflection, the optical fiber including one or more Bragg reflection gratings;
   an acquisition subsystem configured to receive the deflection information from the measurement subsystem and PET measurement data corresponding to a plurality of coincidence events from a PET scanner, and to communicate the received deflection information and PET measurement data to a reconstruction subsystem;
   and the reconstruction subsystem, including a processor configured to reconstruct a PET scan image using the received deflection information and the received PET measurement data.

2. The PET imaging system according to claim 1, wherein the measurement subsystem is configured to estimate the deflection in the patient pallet based on at least one deflection amount detected at a predetermined position of the patient pallet.

3. The PET imaging system according to claim 2, wherein the measurement subsystem is configured to receive reflected light from the optical fiber that includes a plurality of Bragg reflection gratings, and to determine deflection amounts at a plurality of positions in the lengthwise direction of the patient pallet based on wavelengths of the reflected light received from the optical fiber.

4. The PET imaging system according to claim 2, wherein the measurement subsystem is configured to receive reflected light from a plurality of optical fibers, including the optical fiber, that each includes a Bragg reflection grating, and to determine deflection amounts at a plurality of positions in the lengthwise direction of the patient pallet based on wavelengths of the reflected light received from the plurality of optical fibers.

5. The PET imaging system according to claim 2, wherein the measurement subsystem is configured to receive light from one or more optical fibers, including the optical fiber, to measure at least one characteristic of the light received from each of the one or more optical fibers for different deflection amounts in the patient pallet and to generate a table that defines correspondences between at least one characteristic of the light received from each of the one or more optical fibers and the different deflection amounts in the patient pallet.

6. The PET imaging system according to claim 1, wherein the processor is configured to generate a transformation matrix in accordance with the detected deflection.

7. The PET imaging system according to claim 6, wherein the processor is configured to apply the transformation matrix to a temporary PET scan image, reconstructed with the deflection, to generate the reconstructed PET scan image.

8. The PET imaging system according to claim 6, wherein the processor is configured to apply a transpose of the transformation matrix to a reconstruction space, used to reconstruct the PET scan image, to generate a corrected reconstruction space, and to reconstruct the PET scan image based on the corrected reconstruction space.

9. A method of a positron emission tomography (PET) system for reconstructing a PET scan image, the method comprising:
   detecting deflection in a patient pallet based on an optical fiber attached to the patient pallet, the optical fiber including one or more Bragg reflection gratings;
   providing deflection information based on the detected deflection;
   receiving, by an acquisition system, the deflection information from the measurement subsystem and PET measurement data corresponding to a plurality of coincidence events from a PET scanner; and
   reconstructing, by a processor included in a reconstruction subsystem, the PET scan image using the received deflection information and the received PET measurement data.

10. The method according to claim 9, wherein the detecting step comprises: estimating the deflection in the patient pallet based on at least one deflection amount detected at a predetermined position of the patient pallet.

11. The method according to claim 10, wherein the detecting step comprises:
   receiving reflected light from the optical fiber that includes a plurality of Bragg reflection gratings;
   and determining deflection amounts at a plurality of positions in the lengthwise direction of the patient pallet based on wavelengths of the reflected light received from the optical fiber.

12. The method according to claim 10, wherein the detecting step comprises:
   receiving reflected light from a plurality of optical fibers, including the optical fiber, that each includes a Bragg reflection grating;
   and determining deflection amounts at a plurality of positions in the lengthwise direction of the patient pallet based on wavelengths of the reflected light received from the plurality of optical fibers.

13. The method according to claim 10, further comprising:
   receiving light from one or more optical fibers including the optical fiber;
   measuring at least one characteristic of the light received from each of the one or more optical fibers for different deflection amounts in the patient pallet;
   and generating a table that defines correspondences between at least one characteristic of the light received from each of the one or more optical fibers and the different deflection amounts in the patient pallet.

14. The method according to claim 9, wherein the reconstructing step comprises: generating a transformation matrix in accordance with the detected deflection.

15. The method according to claim 14, wherein the reconstructing step comprises: applying the transformation matrix to a temporary reconstructed PET scan image, reconstructed with the deflection, to generate the reconstructed PET scan image.

16. The method according to claim 14, wherein the reconstructing step comprises: applying a transpose of the transformation matrix to a reconstruction space, used to reconstruct the PET scan image, to generate a corrected reconstruction space, and reconstructing the PET scan image based on the corrected reconstruction space.

17. The PET imaging system according to claim 1, wherein the measurement subsystem is configured to detect the deflection of a portion of the patient pallet that corresponds to an area of a patient to be imaged.

18. The method according to claim 10, wherein the detecting step comprises:
   detecting the deflection of a portion of the patient pallet that corresponds to an area of a patient to be imaged.

19. A positron emission tomography (PET) imaging system, comprising:
   a measurement subsystem configured to detect deflection of a portion of a patient pallet that corresponds to an area of a patient to be imaged based on an optical fiber that includes one or more Bragg reflection gratings, and to provide deflection information based on the detected deflection;
   an acquisition subsystem configured to receive the deflection information from the measurement subsystem and PET measurement data corresponding to a plurality of coincidence events form a PET scanner, and to communicate the received deflection information and PET measurement data to a reconstruction subsystem; and
   the reconstruction subsystem, including a processor configured to reconstruct a PET scan image using the received deflection information and the received PET measurement data.

\* \* \* \* \*